Figure 1:
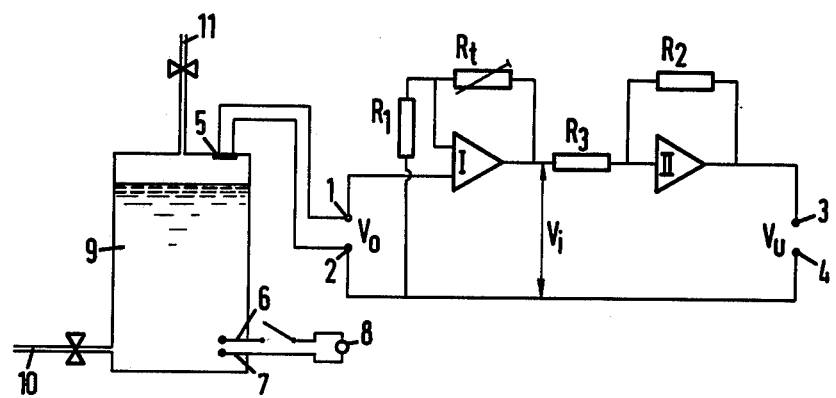

United States Patent [19]
van Strien

[11] 4,179,918
[45] Dec. 25, 1979

[54] METHOD AND AN APPARATUS FOR MEASURING THE CARBON DIOXIDE CONTENT IN BEER

[75] Inventor: Johannes van Strien, Leiden, Netherlands

[73] Assignee: Heineken Technisch Beheer B.V., Netherlands

[21] Appl. No.: 877,090

[22] Filed: Feb. 13, 1978

[51] Int. Cl.² ............................................. G01N 33/14
[52] U.S. Cl. .................................................... 73/19
[58] Field of Search ................. 73/19, 23, 27 R, 61 R, 73/705, 753, 362 AR; 324/65 R

[56] References Cited

U.S. PATENT DOCUMENTS

| | | | |
|---|---|---|---|
| 3,077,765 | 2/1963 | Dijkema | 73/19 |
| 3,609,549 | 9/1971 | Hausler | 324/65 R |
| 3,673,853 | 7/1972 | Griswold et al. | 73/19 |
| 3,861,214 | 1/1975 | Siyahi | 73/362 AR |
| 3,961,247 | 6/1976 | Toki | 324/65 R |

*Primary Examiner*—Stephen A. Kreitman
*Attorney, Agent, or Firm*—Eugene E. Geoffrey, Jr.

[57] ABSTRACT

A method and an apparatus for measuring the carbon dioxide content in beer, in which a beer sample is separated in a vessel and there being created above the beer in the vessel a carbon dioxide atmosphere the pressure of which is measured. A temperature-responsive element is introduced in the beer of which the electric properties similarly vary with the temperature as the Henry constant. An electric signal proportional to the measured pressure is applied to an electric circuit arrangement of which the transfer function depends on the electric properties of the temperature-responsive element. The output signal of the electric circuit arrangement functions as measure for the carbon dioxide content.

7 Claims, 2 Drawing Figures

METHOD AND AN APPARATUS FOR MEASURING THE CARBON DIOXIDE CONTENT IN BEER

The present invention relates to a method of measuring the carbon dioxide content in beer, in which a beer sample is separated in a vessel while above the beer in the vessel there is created a carbon dioxide atmosphere of which the pressure is measured.

It is highly important in the beer preparation that the carbon dioxide content of the beer is maintained at the proper value. A carbon dioxide content that is too low results in the loss of the refreshing effect of the beer, while an excessive carbon dioxide is likewise undesirable.

Consequently it will be clear that it is desirable to have the disposal of a method and an apparatus enabling to measure the carbon dioxide content in a simple manner.

Various apparatuses for measuring the carbon dioxide content in beer are known and the operation of these prior art apparatuses is based on Henry's law, which reads as follows:

"At constant temperature the mass of a gas (for example $CO_2$) dissolved in a given volume of solvent is directly proportional to the partial pressure of said gas above the liquid".

This Henry's law only applies to a closed system when there is equilibrium between the gas in the liquid phase and the gas in the gaseous phase. In symbols the indicated relation can be written as follows:

$$m/V = f \times p \; (T \text{ constant})$$

wherein m=mass of the gass
V=volume of solvent
f=Henry constant
p=pressure
T=temperature in °K.

In this formula the Henry constant f depends on the temperature. Since the temperature of the beer during the preparation may considerably vary, it is necessary to have the disposal of the trend of the Henry constant at varying temperature. For it will then be possible to measure p in the equilibrium condition, multiplying same with the value of the Henry constant at the prevailing temperature (likewise to be measured), determining m/v, e.g. in grams of $CO_2$ per 100 ml of liquid (percent by weight), as conventional in the brewery industry.

Actually various methods and apparatuses for determining the $CO_2$ content in beer are known that make use of the principles above described.

Dutch Pat. No. 267744 discloses a method of measuring the $CO_2$ content in beer, in which a beer sample is separated in a vessel; by means of two electrodes disposed in the vessel, to which a voltage is applied for a short period of time, there is formed a gas atmosphere above the beer; the gas pressure is then measured by means of a pressure gauge. Furthermore the temperature of the beer in the vessel is separately measured, after which the $CO_2$ content is established by means of tables. This prior art method is rather time-consuming and only suitable for gas pressures above 1 atmosphere and therefore does not comply with practical requirements.

German Auslegeschrift No. 2114122 discloses an apparatus for measuring and controlling the carbon dioxide content of beer, in which likewise there is formed a gas atmosphere above beer present in a measuring vessel by means of electrodes, while subsequently the gas pressure is measured. In this prior art apparatus a constant temperature was used as starting point. In practice the temperature of the beer however is not constant, so that the prior art apparatus allows only very inaccurate measurements to be carried out.

In the magazine A.S.B.C. Proceedings, on pp. 111–117 of the 1970 volume, there is described an apparatus for establishing the carbon dioxide content of beer, in which a floating piston suspended between two diaphragms converts the partial gas pressure above a beer sample into a pneumatic signal which is supplied to a pneumatic computer, to which there is likewise applied a temperature signal. The pneumatic computer then calculates the $CO_2$ content of the beer. This apparatus appears to be unsatisfactory in practice, which inter alia is a result of the non-linearity functioning of the employed diaphragms, which is unavoidable in that the floating piston is disposed against the diaphragms.

In "The Brewers Digest" of October 1973, in an article by Paul W. Steen on pp. 54, 55 there is described a process and an apparatus for electronically measuring and controlling the $CO_2$ content of beer, wherein electric signals originating from a pressure converter and a temperature sensor are arranged algebraically, after which the resulting signal is deemed to represent the $CO_2$ content of the beer.

Finally an apparatus for determining the $CO_2$ content in beer is disclosed in Dutch patent application No. 7404619, in which apparatus use is made of a differential pressure meter comprising a diaphragm, the movement of which is measured and represented on a scale. At the one side of said diaphragm prevails the gas equilibrium pressure above a beer sample, and at the other side a correction pressure proportional to the temperature of the beer sample.

It is the object of the present invention to improve and simplify these prior art apparatuses and methods.

To this effect according to the invention a method of the above described type is characterized in that a temperature-responsive element is introduced in the beer in the vessel, the electric properties of the temperature-responsive element varying similarly with the temperature as the Henry constant; that an electric signal directly proportional to the measured pressure is applied to an electric circuit arrangement of which the transfer function depends on the electric properties of the temperature-responsive element; and that the output signal of the electric circuit arrangement is used as measure for the $CO_2$ content.

An apparatus for performing the method according to a further embodiment of the present invention is characterized in that an operational amplifier provided with a feedback loop, comprises a thermistor positioned in the beer in the measuring vessel.

In elucidation of the present invention there will now follow a slightly more elaborate discussion of the properties of the Henry constant f. It appeared from investigations carried out by applicants that the relation between the Henry constant f and the temperature T (°K) can be written as follows:

$$\ln f = -a + (b/T) \tag{1}$$

wherein for a was found: a=10.89232 and for b: b=2654.06. It is observed that this relation between f and T was not known yet from the literature. It was known from the literature though that the relation between the resistor R and the temperature T (°K) of a thermistor can be written as follows:

$$\ln R = -c + (d/T) \quad (2),$$

in which applies for a commercially available thermistor of adequate quality:
c=5.114275 and d=3826.74.

From equations (1) and (2), with the above values for a, b, c, d, it is possible to derive the following linear relation between f and R:

$$f = 3.33 \times 10^{-5} R + 6.86 \times 10^{-2} \quad (3).$$

Starting from the described relation between f and R it is now possible to design a simple electric circuit arrangement which comprises a thermistor present in the beer, and to the input of which there is applied a signal proportional to the partial $CO_2$ gas pressure p above the beer; and supplying to the output a signal that immediately indicates the $CO_2$ content in the beer without the necessity of making allowance for temperature influences.

Figure 2:
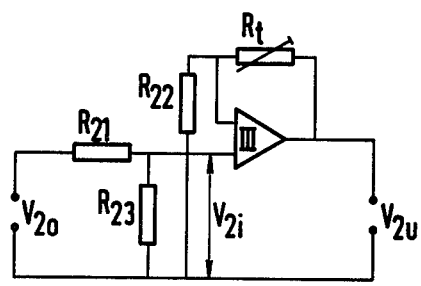

Some embodiments of a circuit arrangement according to the invention will now be described, by way of example, with reference to the accompanying drawings, in which FIG. 1 shows a first embodiment of an apparatus according to the invention and FIG. 2 shows a second embodiment of an apparatus according to the invention.

FIG. 1 shows an operational amplifier I, of which the one input is connected to a first input terminal 1 of the circuit arrangement. The second input terminal 2 is connected to a reference line which is furthermore connected to the one output terminal 4.

Between the input terminals 1 and 2 there is applied a signal voltage $V_o$. Voltage $V_o$ is collected from a pressure-responsive element 5 measuring the partial $CO_2$ pressure above a beer sample. The gas is formed in a known manner, e.g. by shortly applying a voltage between two electrodes 6, 7 present in the beer from an auxiliary voltae source 8. Electrodes 6, 7 and the pressure-responsive element 5 extend in a vessel 9 which is conventionally provided with closable supply and discharge lines 10 and 11.

The other input of the operational amplifier I is connected through an input resistor $R_1$ to the reference line, and through a feedback resistor $R_t$ to the output of the operational amplifier I. The resistor $R_t$ is a temperature-responsive resistor which is disposed in the beer in vessel 9. For clearness' sake resistor $R_t$, however, is drawn in FIG. 1 outside the vessel 9. The resistance value of $R_t$ varies in the above described manner with the temperature and in a practical embodiment of the circuit arrangement the following relation between f and $R_t$ applied:

$$f = 3.33 \times 10^{-5} R_t + 6.86 \times 10^{-2}.$$

It appears from Henry's law that if $V_o$ is proportional to p and moreover f varies similarly with the temperature as $R_t$, the output voltage $V_u$ of the circuit arrangement immediately indicates the $CO_2$ content to be measured, if the gain factor of the amplifier circuitry is conveniently chosen.

For the gain factor $\beta I$ of the operational amplifier I applies:

$$\beta I = \left[ \frac{R_t}{R_1} + 1 \right]$$

Furthermore it applies for a specific type of commercially available pressure-responsive element $V_o = 1.43 \times 10^{-2} p$. It follows therefrom for the output voltage $V_i$ of the first operational amplifier:

$$V_i = V_o \times \beta I = \left[ \frac{R_t}{R_1} + 1 \right] \times 1.43 \times 10^{-2} p \quad (3)$$

The signal $V_i$ is applied through a series resistor to a second amplifier II, the output of which is connected to the output terminal 3 of the circuit arrangement and through a feedback resistor $R_2$ to the input of amplifier II.

The gain factor $\beta II$ of the second amplifier is $\beta II = R_2/R_3$, so that $$V_u = (R_2/R_3)V_i \quad (4).$$

Combination of (3) and (4) gives:

$$V_u = \frac{R_2}{R_3} \left[ \frac{R_t}{R_1} + 1 \right] \times 1.43 \times 10^{-2} p \quad (5)$$

$V_u$ (in volt) is the carbon dioxide content in percent by weight if applies:

$$f = \frac{R_2}{R_3} \left[ \frac{R_t}{R_1} + 1 \right] \times 1.43 \times 10^{-2} =$$

$$3.33 \times 10^{-5} R_t + 6.86 \times 10^{-2}.$$

It follows from the above:

$$\frac{R_2}{R_3} \times \frac{R_t}{R_1} \times 1.43 \times 10^{-2} + \frac{R_2}{R_3} \times 1.43 \times 10^{-2} =$$

$$3.33 \times 10^{-5} R_t + 6.86 \times 10^{-2}. \longrightarrow$$

$$\frac{R_2}{R_3} \times \frac{1}{R_1} \times 1.43 \times 10^{-2} = 3.33 \times 10^{-5} \text{ and}$$

$$\frac{R_2}{R_3} \times 1.43 \times 10^{-2} = 6.86 \times 10^{-2}$$

It was found after some calculation:
$R_1 = 2060 \, \Omega$
$R_2 = 4.797 \, R_3$ FIG. 2 shows a circuit arrangement which is suitable for a different likewise commercially available pressure-responsive element for which applies: $V_{20} = 2.5 \, p$.

This input signal $V_{20}$ is applied through a voltage divider consisting of series resistor $R_{21}$ and a parallel resistor $R_{23}$, to the one input of an amplifier III. The other input of the amplifier is again connected through a resistor $R_{22}$ to the reference line and through a temperature-responsive resistor $R_t$, to the output. If the input signal of amplifier III is indicated by $V_{2i}$ and the output signal by $V_{2u}$, there applies:

$$V_{2i} = \frac{R_{23}}{E_{21} + R_{23}} \times V_{20} = \frac{R_{23}}{R_{21} + R_{23}} \times 2.5p.$$

$V_{2u}$ indicates the carbon dioxide content in percent by weight if:

$$f = \frac{R_{23}}{R_{21} + R_{23}} \left[ \frac{R_t}{R_{22}} + 1 \right] \times 2.5 = 3.33 \times 10^{-5} R_t + 6.86 \times 10^{-2}$$

It follows from the above:

$$\frac{R_{23}}{R_{21} + R_{23}} \times \frac{2.5}{R_{22}} = 3.33 \times 10^{-5} \text{ and}$$

$$\frac{2.5 \cdot R_{23}}{R_{21} + R_{23}} = 6.86 \times 10^{-2}$$

Therefore: $R_{22} = 2060 \, \Omega$ and $R_{21} = 35.44 \, R_{23}$.

Both above described circuit arrangements provide very accurate results over a temperature range covering at least 0°–20° C.

The output voltage $V_u$ or $V_{2u}$ may be rendered in any manner desired, for instance digitally and be used if necessary to control the carbon dioxide supply during the beer preparation process.

It will be clear that the above described method and apparatus may be modified in various manners without departing from the scope of the invention.

I claim:

1. The method of measuring the carbon dioxide content in beer comprising the steps of feeding a beer sample into a vessel to partially fill said vessel and create a carbon dioxide atmosphere above said beer, measuring the temperature of the beer to produce an electric signal which varies with temperature in a manner proportional to changes in a constant f with temperature wherein said constant varies substantially in accordance with the equation $$f = -a + (b/T)$$

wherein:
f = Henry's constant
a = 10.89232
b = 2654.06,
measuring the pressure of said carbon dioxide atmosphere above said beer and producing an electrical signal proportional thereto and combining said signals to produce an output signal which is a direct measure of carbon dioxide content of said beer.

2. The method according to claim 1 wherein said temperature is measured by a thermistor wherein the resistance thereof and the electric signal produced thereby varies linearly with the constant f.

3. The method according to claim 1 wherein said electrical signal proportional to pressure is amplified and the degree of amplification is controlled in accordance with changes in the first said signal.

4. Apparatus for measuring the carbon dioxide content of beer comprising a vessel, means for feeding beer to said vessel to partially fill said vessel and create a carbon dioxide atmosphere above said beer, means for measuring the pressure of said atmosphere and producing an electrical signal proportional thereto, means for measuring the temperature of said beer to provide an electrical signal varying in accordance with changes of a constant f which varies with temperature in accordance with the equation:

$$f = -a + (b/T)$$

wherein:
f = Henry's constant
a = 10.89232
b = 2654.06
means for amplifying the first said signal and a feedback loop including said temperature measuring means on said amplifying means.

5. Apparatus for measuring the carbon dioxide content of beer comprising a vessel, means for feeding beer to said vessel and create a carbon dioxide atmosphere above said beer, means for measuring the pressure of said atmosphere and producing an electrical signal proportional thereto, means for measuring the temperature of said beer to provide an electrical signal varying in accordance with changes of a constant f which varies with temperature in accordance with the equation:

$$f = -a + (b/T)$$

wherein:
f = Henry'constant
a = 10.89232
b = 26543.06
means for amplifying the first said signal and a feedback loop including said temperature measuring means on said amplifying means, said amplifying means includes a final amplifier having an input and output, a second amplifier having an input and output, a resistor coupling the output of the first amplifier with the input of the second amplifier, said feedback loop being about said first amplifier and including means applying a reference voltage to the input thereof and a feedback loop on said second amplifier, the output of said second amplifier representing the carbon dioxide content of the beer.

6. Apparatus for measuring the carbon dioxide content in beer, comprising a vessel, means for feeding a beer sample to said vessel to partially fill said vessel and create a carbon dioxide atmosphere above said beer, a temperature-responsive element for measuring the temperature of the beer in the vessel and producing an electric signal varying with the temperature in accordance with the Henry constant, means for producing an electric signal proportional to the pressure of said atmosphere, an electric circuit and means for feeding said signals to the input of said electric circuit to produce an output signal which is a direct indication of the carbon dioxide content of said beer, said electric circuit including an operational amplifier having a feed back loop between the input and output and said temperature-responsive element is a thermistor forming part of said loop, said feedback loop being connected at the input side of said amplifier through a setting resistor to the reference line, and the output of the amplifier is connected through a series resistor to a second feedback amplifier by means of a resistor, the output of which immediately represents the carbon dioxide content.

7. Apparatus for measuring the carbon dioxide content in beer, comprising a vessel, means for feeding a beer sample to said vessel to partially fill said vessel and create a carbon dioxide atmosphere above said beer, a temperature-responsive element for measuring the temperature of the beer in the vessel and producing an electric signal varying with the temperature in accordance with the Henry constant, means for producing an electric signal proportional to the pressure of said atmosphere, an electric current and means for feeding said signals to the input of said electric circuit to produce an output signal which is a direct indication of the carbon dioxide content of said beer, said electric circuit including an operational amplifier having a feed back loop between the input and output and said temperature responsive element is a thermistor forming part of said loop, said feedback loop being connected at the input side of the amplifier through a setting resistor to the reference line and the pressure signal is applied to the input of the amplifier through a voltage divider formed of two series connected resistors with the junction of said resistors being connected to the amplifier so that the output signal represents the carbon dioxide content of the beer.

* * * * *